United States Patent

Cameron

Patent Number: 5,295,971
Date of Patent: Mar. 22, 1994

[54] IMPACT RELEASABLE POLE MOUNTED SYRINGE

[76] Inventor: Donald Cameron, R.R. #3, Ponoka, Alberta, Canada, T0C 2H0

[21] Appl. No.: 105,287

[22] Filed: Aug. 10, 1993

[51] Int. Cl.⁵ .................................................. A61M 5/00
[52] U.S. Cl. .................................... 604/187; 273/418; 604/143
[58] Field of Search ............... 604/181, 187, 197, 143; 273/418; 102/512

[56] References Cited

U.S. PATENT DOCUMENTS

| | | | |
|---|---|---|---|
| 1,561,854 | 11/1925 | Hein . | |
| 2,168,437 | 8/1939 | Buercklin | 128/218 |
| 2,348,337 | 5/1944 | Francis | 102/92 |
| 2,744,527 | 5/1956 | Barrett et al. | 128/216 |
| 2,854,925 | 10/1958 | Crockford et al. | 102/92 |
| 2,899,960 | 8/1959 | Ginsburg | 128/221 |
| 3,022,785 | 2/1962 | Crockford et al. | 128/218 |
| 3,099,988 | 8/1963 | Ginsburg | 128/221 |
| 3,207,157 | 9/1965 | Murdoch | 128/218 |
| 3,314,286 | 4/1967 | Hickerson et al. | 73/167 |
| 3,334,788 | 8/1967 | Hamilton | 222/43 |
| 3,359,979 | 12/1967 | Murdoch | 128/218 |
| 3,433,223 | 3/1969 | Black | 128/218 |
| 3,605,744 | 9/1971 | Dwyer | 128/218 F |
| 3,721,241 | 3/1973 | Jlohr et al. | 128/221 |
| 3,747,247 | 7/1973 | McNair | 42/1 L |
| 3,780,734 | 12/1973 | Wulff | 128/218 R |
| 3,880,162 | 4/1975 | Simmons | 128/218 R |
| 4,103,893 | 8/1978 | Walker | 273/106.5 D |
| 4,243,036 | 1/1981 | Ott | 128/215 |
| 4,684,366 | 8/1987 | Denny et al. | 604/130 |
| 4,717,384 | 1/1988 | Waldeisen | 604/143 |
| 4,726,594 | 2/1988 | Benke | 273/418 |
| 4,735,611 | 4/1988 | Anderson et al. | 604/130 |
| 4,735,612 | 4/1988 | Chevalier | 604/130 |
| 4,863,428 | 9/1989 | Chevalier | 273/418 |
| 5,202,533 | 4/1993 | Vandersteen | 102/512 |

FOREIGN PATENT DOCUMENTS 1914573  4/1983  U.S.S.R. .

OTHER PUBLICATIONS

Brochure of Cow Poke, Inc.-Air-Powered Pole Syringe.
Brochure of Cap-Chur-pp. 7 and 17 Re: Syringes.

Primary Examiner—John G. Weiss
Attorney, Agent, or Firm—Davis, Bujold & Streck

[57] ABSTRACT

An impact releasable pole mounted syringe is described which includes a pole member having a gripping end and a syringe attachment end. The syringe attachment end has a receptacle with an opening adapted to telescopically receive a syringe. The pole member has a flexible finger protruding past the syringe attachment end and biased radially away from the pole member. The finger has an engagement member positioned at a remote end. A syringe is provided having a plunger end and a needle end. The plunger end is adapted for telescopic insertion into the receptacle at the syringe attachment end of the pole member. The syringe has an annular collar serving as a stop to limit the telescopic insertion of the syringe into the receptacle. The syringe has an engagement channel adapted to receive the engagement member. A pressure sensitive stop is provided to maintain the syringe and the pole member in the engaged position wherein the engagement member is engaged with the engagement channel to couple the syringe with the pole member. Upon an axial pressure being placed upon the needle end of the syringe the pressure sensitive stop permits the syringe to travel further into the receptacle of the pole member, moving the engagement member along the engagement channel until it is released. Upon the engagement member being released from the engagement channel the biased finger springs radially away from the pole member permitting unrestricted withdrawal of the syringe from the receptacle.

8 Claims, 2 Drawing Sheets

5,295,971

IMPACT RELEASABLE POLE MOUNTED SYRINGE

The present invention relates to an impact releasable pole mounted syringe.

BACKGROUND OF THE INVENTION

When giving animals injections, syringes containing medication are often mounted on poles. The purpose of mounting the syringe onto a pole is to provide a greater reach to a farmer or rancher endeavouring to administer an injection to an animal. Without the use of a pole or some form of projectile it is extremely difficult to get close enough to an animal to administer an injection.

Once a needle from a pole mounted syringe is inserted into an animal's hide, the animal has a tendency to bolt. If the farmer or rancher continues to hold onto the pole when the animal bolts, the needle is withdrawn prematurely leaving unadministered medication in the syringe. If the farmer or rancher lets go of the pole, the pole will be dragged along the ground, which will also withdrawn the needle prematurely from the animal's hide.

Attempts have been made to develop impact releasable pole mounted syringes. An example of such an impact releasable pole mounted syringe is U.S. Pat. No. 4,684,366 which issued to Denny et al in 1987. The Denny reference discloses a pole with a retractable collar at one end having a plurality of integral spring triggers. A syringe is inserted part way into a remote end of the retractable collar. The other end of the retractable collar has a spring biased plunger which is maintained in a compressed condition by the triggers. The interior surfaces of each of the triggers are bevelled and act like cam surfaces. Upon impact with an animal, the syringe to forced all the way into the retractable collar. As the syringe moves into the retractable collar, it engages the bevelled cam surfaces on the interior of the triggers forcing the triggers outwardly. With the triggers forced outwardly, the plunger is no longer constrained and is urged by the biasing force of the spring forward to jettison the retractable collar. The problem with the release mechanism as taught by Denny et al is it's complexity.

SUMMARY OF THE INVENTION

What is required is an alternate form of impact releasable pole mounted syringe.

According to the present invention there is provided an impact releasable pole mounted syringe which includes a pole member having a gripping end and a syringe attachment end. The syringe attachment end has a receptacle with an opening adapted to telescopically receive a syringe. The pole member has a flexible finger protruding past the syringe attachment end and biased radially away from the pole member. The finger has an engagement member positioned at a remote end. A syringe is provided having a plunger end and a needle end. The plunger end is adapted for telescopic insertion into the receptacle at the syringe attachment end of the pole member. The syringe has an annular collar serving as stop means to limit the telescopic insertion of the syringe into the receptacle. The syringe has an engagement channel adapted to receive the engagement member. Pressure sensitive stop means are provided to maintain the syringe and the pole member in the engaged position wherein the engagement member is engaged with the engagement channel to couple the syringe with the pole member. Upon an axial pressure being placed upon the needle end of the syringe the pressure sensitive stop means permits the syringe to travel further into the receptacle of the pole member. This moves the engagement member along the engagement channel until it is released from the engagement channel. Upon the engagement member being released from the engagement channel the biased finger springs radially away from the pole member permitting unrestricted withdrawal of the syringe from the receptacle.

The impact releasable pole mounted syringe, as described, is of relatively simple construction. There are a variety of various types of engagement member and engagement channels which can be successfully used; two of which will hereinafter be further described.

There are, similarly, various configurations of pressure sensitive stop means which can be successfully used. The preferred form of pressure sensitive stop means includes an annular sleeve on the syringe terminating in an annular shoulder with a cam surface. The shoulder engages a peripheral edge of the opening to the receptacle to maintain the syringe in the engaged position. Upon pressure being exerted upon the syringe the cam surfaces pass along the peripheral edges until the sleeve enters the receptacle thereby releasing the biased finger from the groove to spring radially away from the pole member permitting unrestricted withdrawal of the syringe from the receptacle.

BRIEF DESCRIPTION OF THE DRAWINGS

These and other features of the invention will become more apparent from the following description in which reference is made to the appended drawings, wherein.

DETAILED DESCRIPTION OF THE PREFERRED EMBODIMENT

Figure 1:
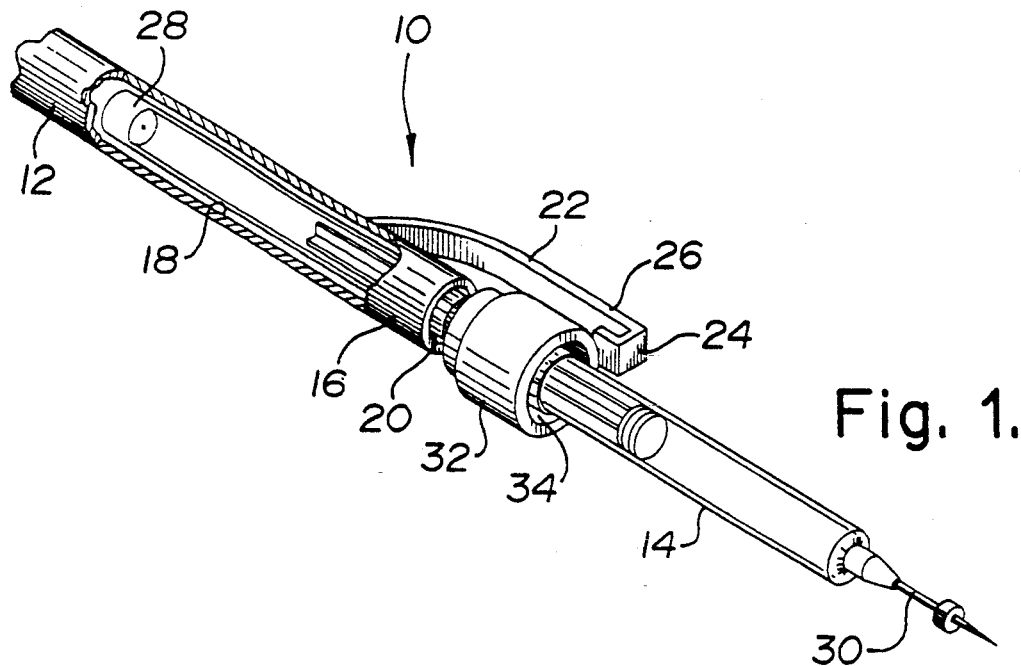
FIG. 1 is a perspective view of a pole mounted syringe constructed in accordance with the teachings of the present invention.

The preferred embodiment, an impact releasable pole mounted syringe generally identified by reference numeral 10, will now be described with reference to FIGS. 1 through 4.

Figure 2:
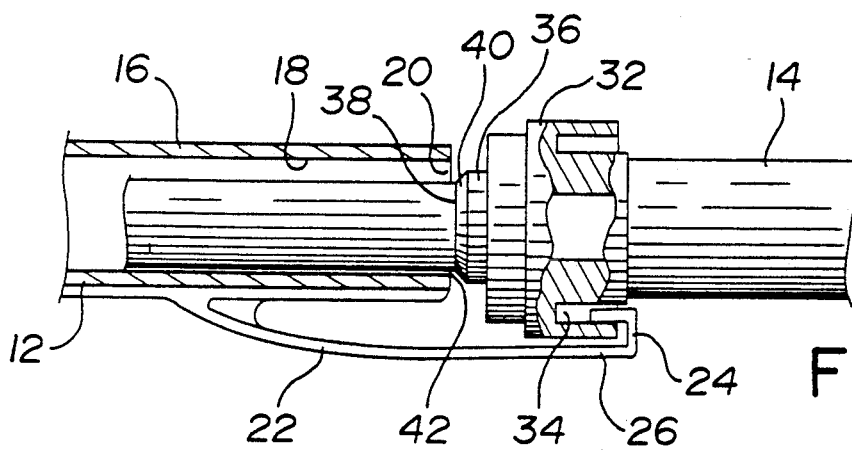
FIG. 2 is a partially cut away side elevation view of the pole mounted syringe illustrated in FIG. 1.
Figure 3:
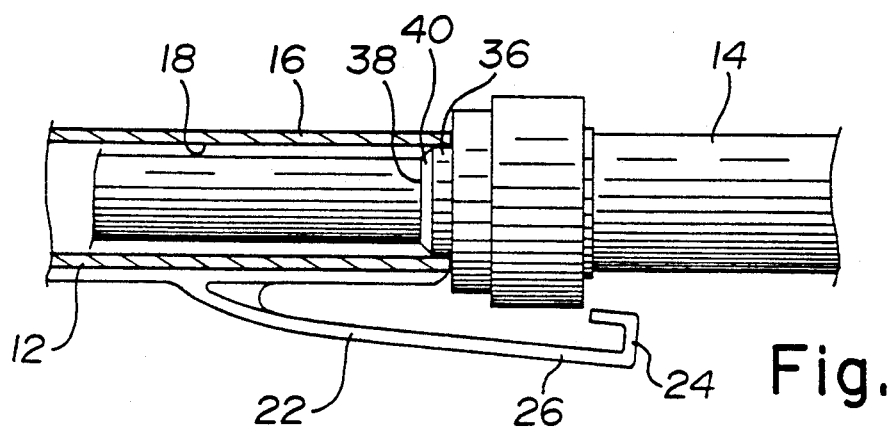
FIG. 3 is a side elevation view of the pole mounted syringe illustrated in FIG. 1.

Referring to FIG. 1, impact releasable pole mounted syringe 10 includes a pole member 12 and a syringe 14. Pole member 12 has a gripping end (not shown) and a syringe attachment end 16. Syringe attachment end 16 has a receptacle 18 with an opening 20 adapted to telescopically receive syringe 14. Pole member 12 has a flexible finger 22 protruding past syringe attachment end 16 and biased radially away from pole member 12. Finger 22 has a hook-like engagement member 24 positioned at a remote end 26. Syringe 14 has a plunger end 28 and a needle end 30. Plunger end 28 is adapted for telescopic insertion into receptacle 18 at syringe attachment end 16 of pole member 12. Syringe 14 has an annular collar 32 serving as stop means to limit the telescopic insertion of syringe 14 into receptacle 18. Syringe 14 has an engagement channel 34 disposed between annular collar 32 and syringe 14. Engagement channel 34 faces needle end 30 of syringe 14 and is adapted to receive hook-like engagement member 24. Referring to FIGS. 2 and 3, a pressure sensitive stop is provided in the form of an annular sleeve 36 on syringe 14 terminating in an annular shoulder 38 with a cam surface 40. Shoulder 38 engages a peripheral edge 42 of opening 20 to receptacle 18 to maintain syringe 14 in an engaged position wherein hook-like engagement member 24 is engaged with engagement channel 34 to couple syringe 14 with pole member 12, as illustrated in FIG. 2.

The use and operation of impact releasable pole mounted syringe 10 will now be described with reference to FIGS. 1 through 3. Hook-like engagement member 24 is positioned in engagement channel 34. In this engaged position syringe 14 is secured to pole member 12. Upon an axial pressure being exerted upon syringe 14 at the time of an injection, cam surfaces 40 pass along peripheral edge 42 of opening 20 until sleeve 36 enters receptacle 18. Once sleeve 36 enters receptacle 18 syringe 14 can travel further into receptacle 18 until annular collar 32 is encountered. As syringe 14 moves further into receptacle 18 of pole member 12 hook-like engagement member 24 moves along engagement channel 34 until it is released. With engagement member 24 released from engagement channel 34, biased finger 22 springs radially away from pole member 12 permitting unrestricted withdrawal of syringe 14 from receptacle 18. Usually a line will be attached to syringe 14, so that syringe 14 can be recovered after the medication is administered by pulling on the line. Syringe 14 is usually pressurized to expel its contents upon insertion.

Figure 4:
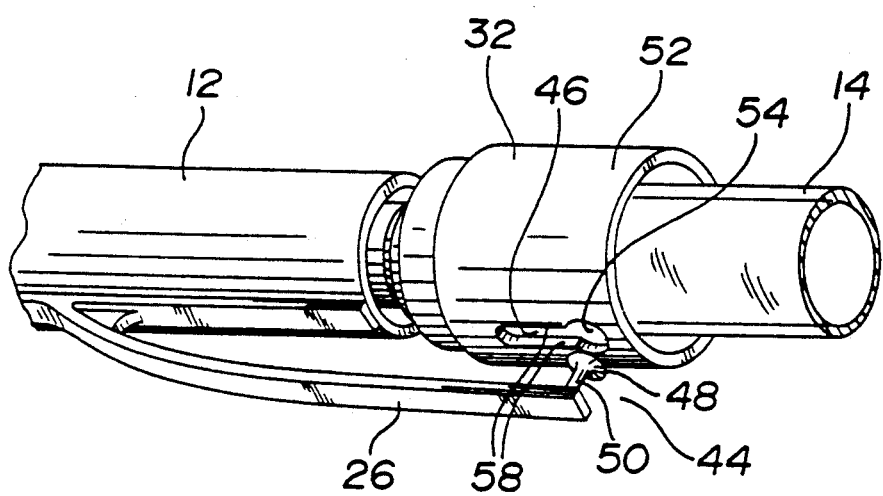
FIG. 4 is a side elevation view of an alternative embodiment of pole mounted syringe.

Referring to FIG. 4, there is illustrated an engagement member 44 which is an alternative to hook-like engagement member 24 and an engagement channel 46 which is an alternative to engagement channel 34. Engagement member 44 has a head portion 48 and a neck portion 50. Engagement channel 46 is positioned on an exterior surface 52 of annular collar 32. Engagement channel 46 is elongate with an enlarged opening 54 at one end 56 and peripheral flanges 58. In order to place engagement member 44 into an engaged position head portion 48 of engagement member 44 is inserted through enlarged opening 54 into engagement channel 46. Once head portion 48 is in engagement channel 46, peripheral flanges 58 confine head portion 48 and prevent it from being withdrawn. When axial pressure is placed upon syringe 14 head portion 48 slides along engagement channel 46 until it is aligned with enlarged opening 54, at which point it is withdrawn through enlarged opening 54 by the biasing force of finger 22.

It will be apparent to one skilled in the art that modifications may be made to the illustrated embodiments without departing from the spirit and scope of the invention as defined by the claims.

I claim:

1. An impact releasable pole mounted syringe, comprising:
  a. a pole member having a gripping end and a syringe attachment end, the syringe attachment end having a receptacle with an opening to telescopically receive a syringe, the pole member having a flexible finger protruding past the syringe attachment end and biased radially away from the pole member, the finger having an engagement member positioned at a remote end;
  b. said syringe having a plunger end and a needle end, the plunger end being telescopically insertable into the receptacle at the syringe attachment end of the pole member, the syringe having an annular collar serving as stop means to limit the telescopic insertion of the syringe into the receptacle, the syringe having an engagement channel adapted to receive the engagement member; and
  c. pressure sensitive stop means maintaining the syringe and the pole member in an engaged position wherein the engagement member is engaged with the engagement channel to couple the syringe with the pole member, upon an axial pressure being placed upon the syringe the pressure sensitive stop means permitting the syringe to travel further into the receptacle of the pole member thereby moving the engagement member along the engagement channel until it is released from the engagement channel such that the biased finger springs radially away from the pole member permitting unrestricted withdrawal of the syringe from the receptacle.

2. The impact releasable pole mounted syringe as defined in claim 1, the engagement member being hook-like.

3. The impact releasable pole mounted syringe as defined in claim 1, the engagement member having a head portion and a neck portion.

4. The impact releasable pole mounted syringe as defined in claim 2, the engagement channel being disposed between the annular collar and the syringe, the engagement channel facing the needle end of the syringe and being adapted to receive the hook-like engagement member.

5. The impact releasable pole mounted syringe as defined in claim 3, the engagement channel being on the exterior surface of the annular collar, the engagement channel being elongate with an enlarged opening at one end adapted to receive the head portion of the engagement member for insertion in the engagement channel and peripheral flanges adapted to confine the head portion of the engagement member when it is positioned in the engagement channel.

6. The impact releasable pole mounted syringe as defined in claim 1, the pressure sensitive stop means being an annular sleeve on the syringe terminating in an annular shoulder with a cam surface, the shoulder engaging a peripheral edge of the opening to the receptacle to maintain the syringe in the engaged position, upon pressure being exerted upon the syringe the cam surface pass along the peripheral edge until the sleeve enters the receptacle thereby releasing the biased finger from the engagement channel to spring radially away from the pole member permitting unrestricted withdrawal of the syringe from the receptacle.

7. An impact releasable pole mounted syringe, comprising:
  a. a pole member having a gripping end and a syringe attachment end, the syringe attachment end having a receptacle with an opening to telescopically receive a syringe, the pole member having a flexible finger protruding past the syringe attachment end and biased radially away from the pole member, the finger having a hook-like engagement member positioned at a remote end;
  b. said syringe having a plunger end and a needle end, the plunger end being telescopically insertable into the receptacle at the syringe attachment end of the pole member, the syringe having an annular collar serving as stop means to limit the telescopic insertion of the syringe into the receptacle, the syringe having an engagement channel disposed between the annular collar and the syringe, the engagement channel facing the needle end of the syringe and being adapted to receive the hook-like engagement member; and c. a pressure sensitive stop in the form of an annular sleeve on the syringe terminating in an annular shoulder with a cam surface, the shoulder engaging a peripheral edge of the opening to the receptacle to maintain the syringe in an engaged position wherein the engagement member is engaged with the engagement channel to couple the syringe with the pole member, upon an axial pressure being exerted upon the syringe the cam surface pass along the peripheral edge until the sleeve enters the receptacle permitting the syringe to travel further into the receptacle of the pole member thereby moving the engagement member along the engagement channel until it is released from the engagement channel such that the biased finger springs radially away from the pole member permitting unrestricted withdrawal of the syringe from the receptacle.

8. An impact releasable pole mounted syringe, comprising:

a. a pole member having a gripping end and a syringe attachment end, the syringe attachment end having a receptacle with an opening to telescopically receive a syringe, the pole member having a flexible finger protruding past the syringe attachment end and biased radially away from the pole member, the finger having an engagement member positioned at a remote end, the engagement member having a head portion and a neck portion;

b. said syringe having a plunger end and a needle end, the plunger end being telescopically insertable into the receptacle at the syringe attachment end of the pole member, the syringe having an annular collar serving as stop means to limit the telescopic insertion of the syringe into the receptacle, the syringe having an engagement channel on the exterior surface of the annular collar, the engagement channel being elongate with an enlarged opening at one end adapted to receive the head portion of the engagement member for insertion in the engagement channel and peripheral flanges adapted to confine the head portion of the engagement member when it is positioned in the engagement channel; and c. a pressure sensitive stop in the form of an annular sleeve on the syringe terminating in an annular shoulder with a cam surface, the shoulder engaging a peripheral edge of the opening to the receptacle to maintain the syringe in an engaged position wherein the engagement member is engaged with the engagement channel to couple the syringe with the pole member, upon an axial pressure being exerted upon the syringe the cam surface pass along the peripheral edge until the sleeve enters the receptacle permitting the syringe to travel further into the receptacle of the pole member thereby moving the engagement member along the engagement channel until it is released from the engagement channel such that the biased finger springs radially away from the pole member permitting unrestricted withdrawal of the syringe from the receptacle.

* * * * *